United States Patent
Divino, Jr. et al.

(10) Patent No.: US 6,558,502 B2
(45) Date of Patent: May 6, 2003

(54) METHOD FOR FORMING ATRAUMATIC FLUID DELIVERY DEVICE

(75) Inventors: Vincent Divino, Jr., Mission Viejo, CA (US); John Merritt, San Clemente, CA (US); Seth A. Foerster, San Clemente, CA (US); William C. Homet, San Juan Capistrano, CA (US); Paul J. Zalesky, Huntington Beach, CA (US)

(73) Assignee: TherOx, Inc., Irvine, CA (US)

( * ) Notice: Subject to any disclaimer, the term of this patent is extended or adjusted under 35 U.S.C. 154(b) by 0 days.

(21) Appl. No.: 09/859,122

(22) Filed: May 16, 2001

(65) Prior Publication Data

US 2002/0040232 A1 Apr. 4, 2002

Related U.S. Application Data

(60) Division of application No. 09/092,254, filed on Jun. 5, 1998, now Pat. No. 6,235,007, which is a continuation-in-part of application No. 08/669,662, filed on Jun. 24, 1996, now Pat. No. 5,957,899, which is a continuation-in-part of application No. 08/563,057, filed on Nov. 27, 1995, now Pat. No. 5,797,876.

(51) Int. Cl.[7] ............................................. A61M 25/09
(52) U.S. Cl. ..................... 156/294; 156/256; 156/303.1
(58) Field of Search ............................. 156/293, 303.1, 156/294, 256, 272.8; 604/528; 600/585; 228/131

(56) References Cited

U.S. PATENT DOCUMENTS

| | | | |
|---|---|---|---|
| 4,793,350 A | 12/1988 | Mar et al. .................. 128/344 |
| 4,964,409 A | 10/1990 | Tremulis .................... 128/657 |
| 5,067,489 A | 11/1991 | Lind ........................... 128/772 |
| 5,087,244 A | 2/1992 | Wolinsky et al. ............. 604/53 |
| 5,158,548 A | 10/1992 | Lau et al. ..................... 604/96 |
| 5,322,508 A | 6/1994 | Viera ........................... 604/52 |
| 5,324,263 A | 6/1994 | Kraus et al. .................. 604/96 |
| 5,376,083 A | 12/1994 | Mische ........................ 604/264 |
| 5,395,353 A | 3/1995 | Scribner ...................... 604/264 |
| 5,569,197 A | 10/1996 | Helmus et al. ............... 604/96 |
| 5,599,296 A | 2/1997 | Spears ......................... 604/26 |
| 5,605,162 A | 2/1997 | Mirzaee et al. ............. 128/772 |
| 5,628,755 A | 5/1997 | Heller et al. ................. 606/108 |
| 5,634,897 A | 6/1997 | Dance et al. ................. 604/35 |
| 5,702,364 A | 12/1997 | Euteneuer et al. ........... 604/96 |
| 5,935,122 A | 8/1999 | Fourkas et al. ............. 604/523 |
| 5,989,210 A | 11/1999 | Morris et al. ................ 604/22 |

FOREIGN PATENT DOCUMENTS

| | | | | |
|---|---|---|---|---|
| EP | 0 490 459 A1 | 6/1992 | .......... | A61M/25/00 |
| WO | WO 97/11735 | 4/1997 | .......... | A61M/25/00 |
| WO | WO 97/49447 | 12/1997 | .......... | A61M/25/00 |

*Primary Examiner*—Michael W. Ball
*Assistant Examiner*—Todd J. Kilkenny
(74) *Attorney, Agent, or Firm*—Margaret A. Kivinski

(57) ABSTRACT

The present invention is a device for insertion into a human or animal body, in a preferred embodiment a perfusion guidewire capable of delivering perfusion fluids to a vascular site while at the same time exhibiting handling characteristics associated with existing non-perfusion guidewires. Preferred embodiments include a perfusion guidewire which closely matches the dimensions and physical characteristics of standard guidewires. Preferred embodiments also permit high pressure perfusion of oxygen-supersaturated solutions, and include a diffuser segment which divides the flow and reduces fluid velocity, thereby providing an atraumatic, non-cavitating, bubble-free delivery to the patient. The invention also encompasses the attachment of a core wire within a tubular housing to provide superior characteristics to such guidewires, balloon catheters and similar devices.

20 Claims, 6 Drawing Sheets

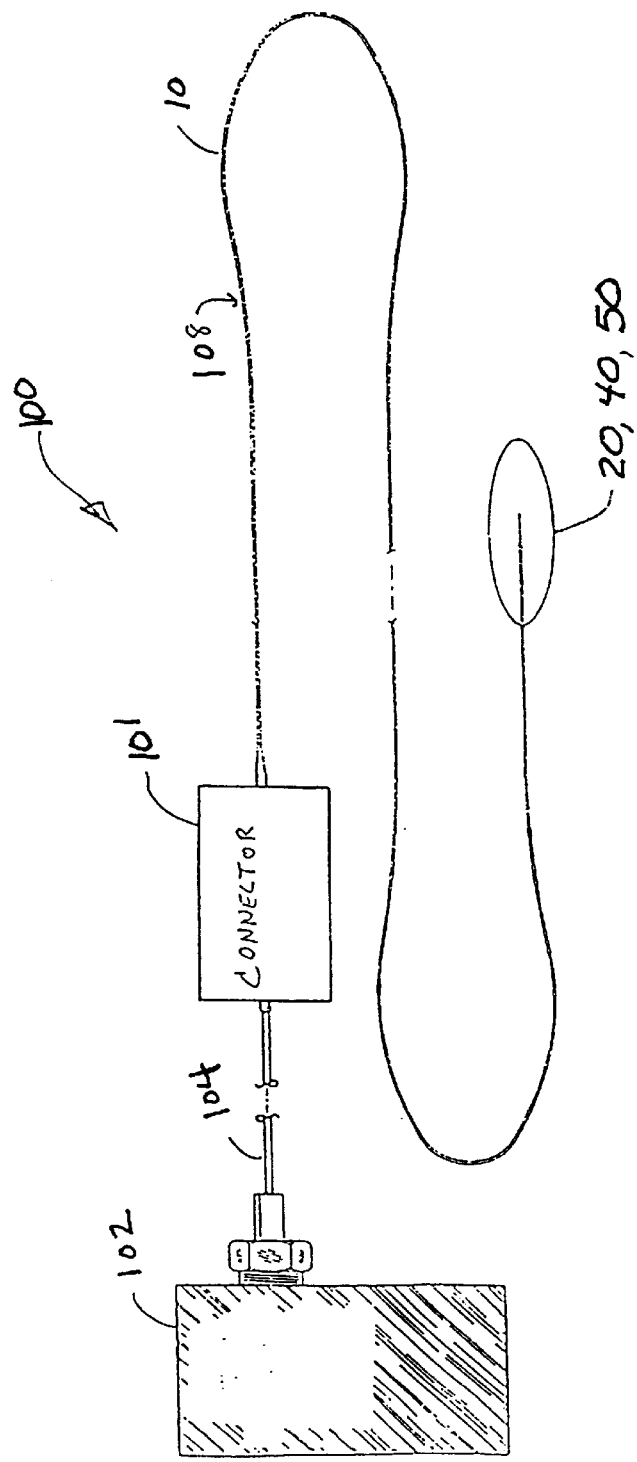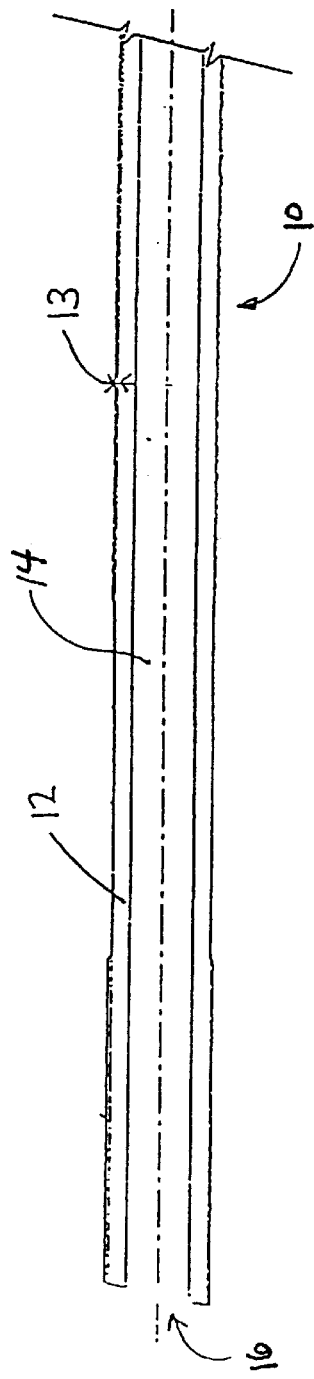

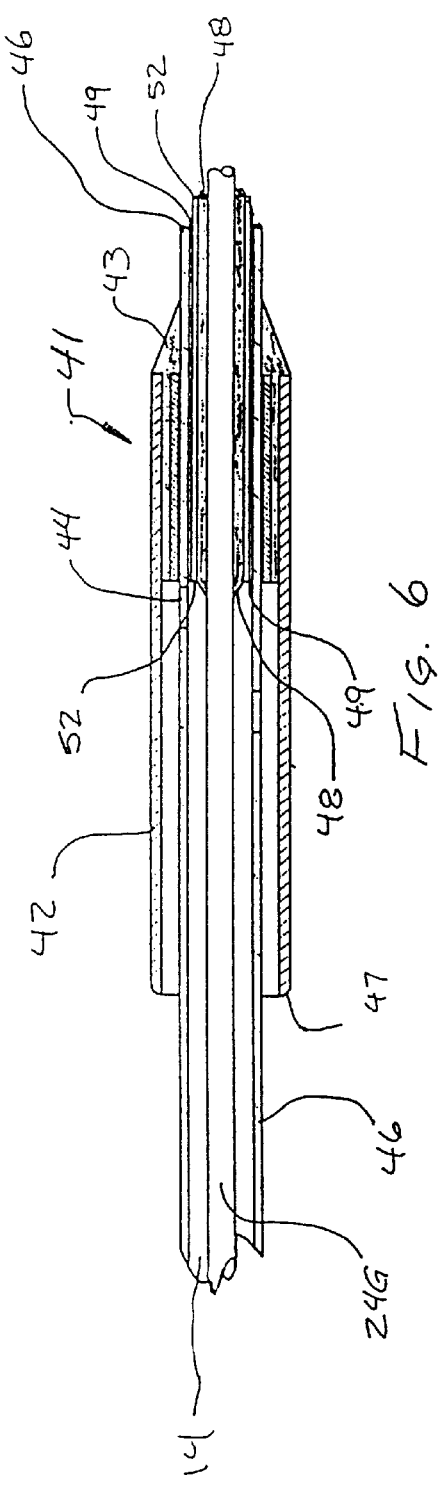
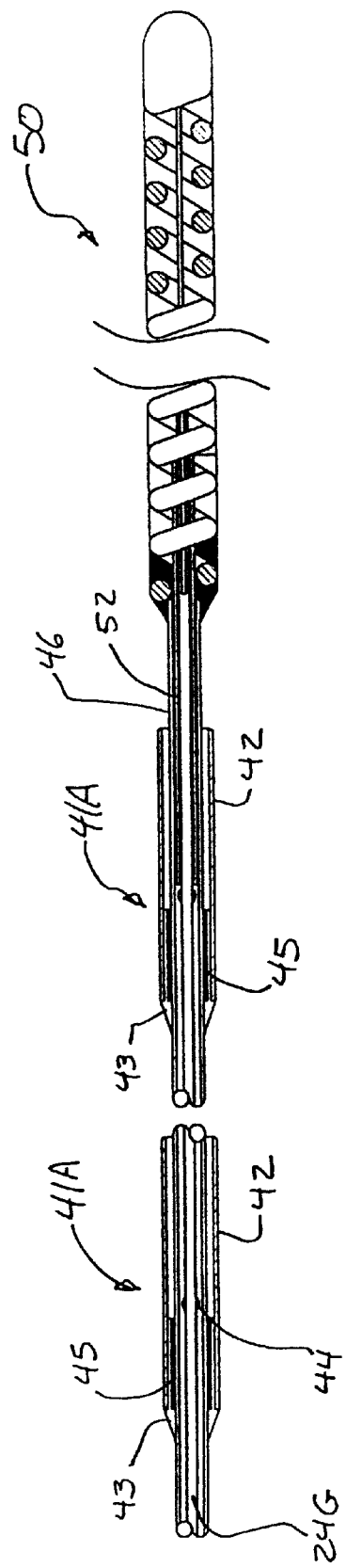
FIG. 6
FIG. 7A

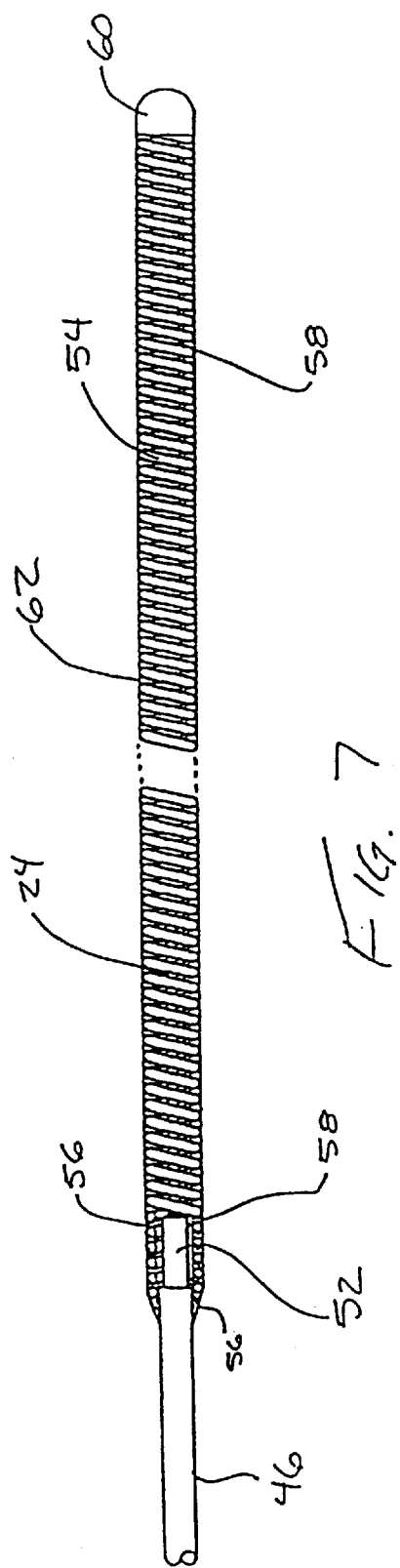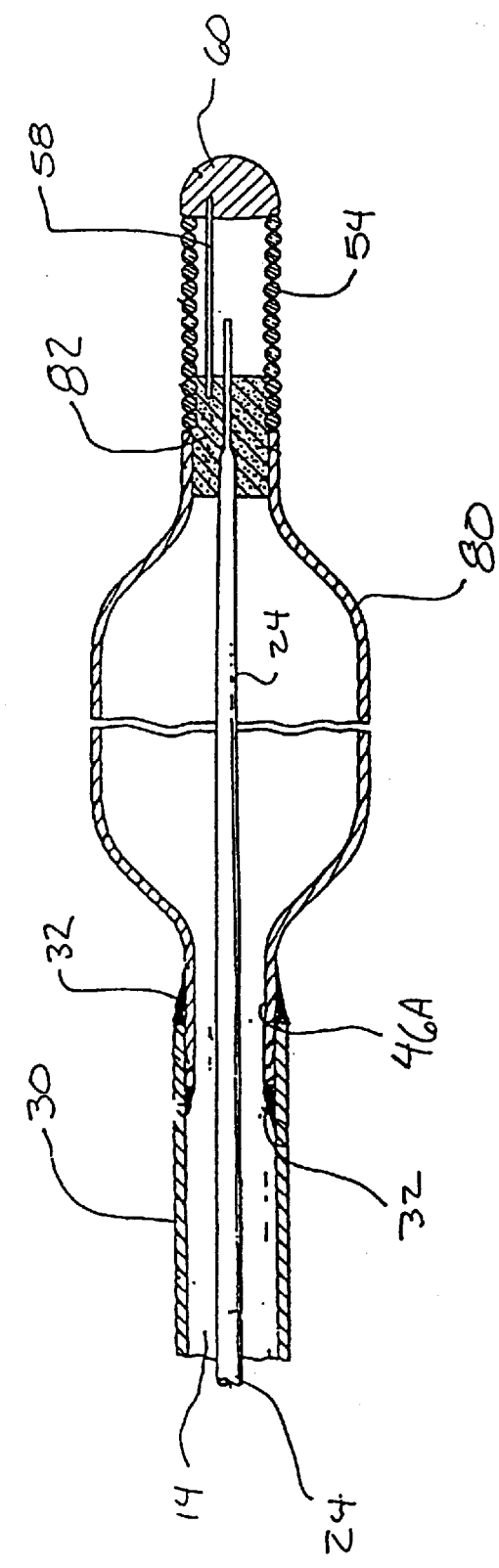

METHOD FOR FORMING ATRAUMATIC FLUID DELIVERY DEVICE

RELATED APPLICATIONS

This application is a divisional of U.S. patent application Ser. No. 09/092,254, filed Jun. 5, 1998, (now U.S. Pat. No. 6,235,007 B1,) which is a continuation-in-part of U.S. patent application Ser. No. 08/669,662, filed Jun. 24, 1996 (now U.S. Pat. No. 5,957,899), which is a continuation-in-part of U.S. patent application Ser. No. 08/563,057, filed Nov. 27, 1995 (now U.S. Pat. No. 5,797,876), all of which are incorporated herein by reference.

BACKGROUND

The present invention relates generally to medical devices for insertion into the human or animal body and more particularly to guiding members with central lumens, particularly perfusion devices and balloons. Even more particularly, the present invention relates to a perfusion guidewire capable of delivering gas supersaturated solutions at high pressure atraumatically and bubble-free.

Various medical procedures require fluids to be delivered to specific locations within the body, typically via a fluid delivery catheter. A narrow steerable guidewire is often used to maneuver through narrow, tortuous, and/or branching body passageways. After the guidewire has been directed to the desired location, a fluid delivery catheter may be inserted over the guidewire. The guidewire is usually removed before fluid delivery begins. Alternatively, guidewires which are themselves capable of fluid delivery are also known in the art. Examples of such guidewires are disclosed in U.S. Pat. Nos. 4,964,409 and 5,322,508. Although the devices disclosed in these two patents do not appear to have been commercialized, it would appear that both would suffer from similar drawbacks in manufacturability and handling characteristics due to the manner in which the core wire is attached within each device.

Another application of such fluid delivery devices is in balloon angioplasty and similar procedures. In balloon angioplasty, a catheter equipped with a small balloon is inserted (usually over a guidewire) into an artery that has been narrowed, typically by the accumulation of fatty deposits. The balloon is then inflated to clear the blockage or lesion and widen the artery. During balloon inflation, blood flow distal to (i.e., "downstream" from) the inflated balloon may be completely or almost completely blocked.

Myocardial ischemia (i.e., a reduction in blood perfusion to the heart muscle) occurs transiently in many patients undergoing coronary angioplasty procedures, such as balloon angioplasty, directional atherectomy, rotational atherectomy, and stent deployment. The permissible duration of occlusion due to balloon inflation or other device deployment is normally determined by the severity of myocardial ischemia. Typically, evidence of severe ischemia (including patient chest pain and ECG changes) requires that the operator deflate the balloon or remove the occlusive device after approximately 60 to 120 seconds. For anatomically difficult lesions, such as type B and C lesions, longer periods of balloon inflation (or other device deployment) are frequently desirable for the first balloon inflation or other device deployment.

Autoperfusion balloon catheters can in some circumstances allow longer periods of balloon inflation. However, the blood (or other physiologic liquid) flow through such devices is frequently insufficient to provide an adequate oxygen supply to tissues distal to the angioplasty balloon or other occlusive device.

Recent advances in the generation and delivery of supersaturated oxygen solutions have made it possible to deliver greater amounts of oxygen to tissues distal to an angioplasty balloon. For example, U.S. Pat. No. 5,407,426, entitled "Method for Delivering a Gas-Supersaturated Fluid to a Gas-Depleted Site and Use Thereof" and U.S. Pat. No. 5,599,296 entitled "Apparatus and Method of Delivery of Gas-Supersaturated Liquids" disclose various methods for the generation and delivery of supersaturated oxygen solutions.

As is described in the two above patents, the generation, transport, and delivery of supersaturated oxygen solutions may require the application of high hydrostatic pressures. Accordingly, there is a need for a high pressure device capable of infusing bubble-free fluid, which is supersaturated at high pressures (preferably with oxygen), to vessels or ducts through and beyond the central lumen of a balloon angioplasty catheter or similarly occlusive device. There is a further need for a high pressure guidewire capable of delivering such supersaturated oxygen solutions to small vessels without rupturing or otherwise damaging those vessels. The guidewire disclosed in the '508 and '409 patents referenced above would not be well suited to such applications for a variety of reasons. For example, the internal fluid lumens and fluid exits are not configured to eliminate bubble formation which can result from the delivery of gas supersaturated liquids. Bubble formation in the coronary arteries can be fatal. Also these devices are not designed to handle the high pressures necessary for adequate oxygen delivery while maintaining an a traumatic flow out of the device. There thus remains a need in the art for a fluid delivery device with standard guidewire handling characteristics capable of atraumatically delivering gas supersaturated fluids at high pressure into tortuous vasculature.

SUMMARY OF THE INVENTION

Accordingly, it is an object of the present invention to provide a guidewire capable of delivering perfusion fluids to a vascular site while at the same time exhibiting handling characteristics associated with existing non-perfusion guidewires so that additional education or retraining of operators is reduced or eliminated.

It is a further object of the present invention to provide a guidewire capable of delivering supersaturated solutions at high pressures to vessels or ducts atraumatically.

A preferred embodiment of the present invention meets the foregoing needs by providing a perfusion guidewire which closely matches the dimensions and physical characteristics of standard guidewires in diameter, length, flexibility, column strength, torque transfer, surface friction, kink resistance, radiopacity (i.e., opacity to x-rays), non-thrombogenicity (i.e., tendency not to promote blood clots) and bio-compatibility. A preferred embodiment of the invention includes a diffuser which provides bubblefree injection of metastable supersaturated solutions. The diffuser is provided with sleeves positioned so that the rapid flow from the diffuser is deflected axially along the device to protect vessels from rupture. A perfusion guidewire according to the present invention preferably includes four general sections: a tubular proximal segment, which comprises the greater part of the perfusion guidewire length; a transitional region which provides for attachment of the core wire such that the fluid delivery requirements are met without compromising guidewire handling; a distal diffuser segment which provides a pressure and velocity drop for the delivered fluid and serves to optimally deflect fluid flow; and a coil tip which mimics the distal functions of a standard coronary guidewire. A further aspect of the present invention includes a method of attaching a core wire to a tubular housing in a fluid delivery guidewire or other device. A preferred embodiment of the method includes forming a side hole in the tubular housing, passing an end of the core wire through the hole in the tubular housing, melting a ball on the end of the core wire, pulling the core wire to position the ball against the tubular housing and welding it in place.

BRIEF DESCRIPTION OF THE DRAWINGS

Reference is next made to a brief description of the drawings, which illustrate an exemplary embodiment of a perfusion guidewire according to the present invention. The drawings and detailed description which follow are intended as an example of the present invention, the scope of which is set forth in the appended claims.

FIG. 1 illustrates a transluminal fluid delivery system including a fluid delivery device according to an embodiment of the present invention;

FIG. 2 is a cross-sectional view of the proximal portion or handle of a perfusion guidewire according to an embodiment of the present invention;

FIG. 6 is an enlarged, partial cross-sectional view of the distal diffuser identified by circle 6 in FIG. 3; and FIG. 7 is a partial cross-sectional view of the distal tip of a perfusion guidewire according to the present invention;

FIG. 7A is a partial cross-sectional view of a portion of a perfusion guidewire showing an alternative diffuser segment and a distal tip according to an alternative embodiment of the invention;

FIG. 9 is a cross-sectional view of the distal end of a balloon catheter according to the present invention.

DETAILED DESCRIPTION

Figure 3:
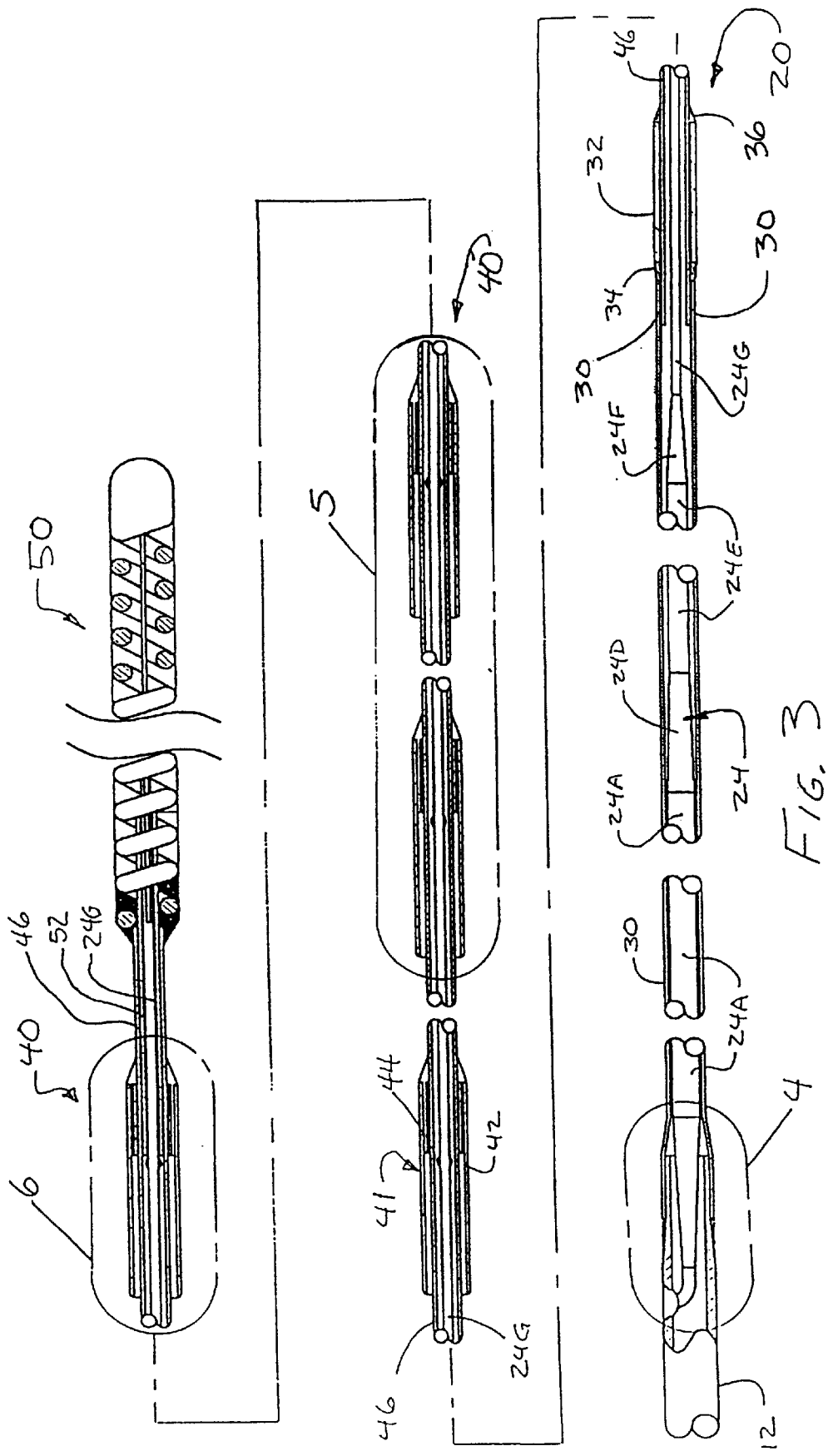
FIG. 3 is a partial cross-sectional view of the distal part of a perfusion guidewire according to the invention.

The structure and function of the preferred embodiments can best be understood by reference to the drawings where the same reference numerals appear in multiple figures, the numerals refer to the same or corresponding structure in those figures.

FIG. 1 shows a transluminal fluid delivery system 100 including a perfusion guidewire according to the present invention. Fluid delivery system 100 includes a source of supersaturated fluid at high pressure 102, such as a pump or reservoir, connector 101, tube 104 connecting an output of fluid source 102 to an input of connector 101, and high pressure delivery device 108, which will be described according to the present invention in terms of a preferred embodiment as a coronary guidewire. As will be discussed further below, perfusion guidewire 108 includes proximal segment 10, transitional region 20, distal diffuser segment 40, and coil tip 50.

In preferred embodiments of the invention, fluid source 102 will provide oxygen supersaturated liquid (such as physiologic saline) at high pressure and under conditions which maintain the oxygen in solution without bubble formation. An example of a fluid source is described in U.S. Pat. No. 5,599,296 entitled "Apparatus and Method of Delivery of Gas-Supersaturated Liquids". Utilizing such a system, generation and delivery of oxygen-supersaturated fluids at pressures from about 100 to 10,000 psi, with oxygen concentrations of about 0.1 to 2 cc $O_2$/g, are achievable. The device according to the present invention is preferably capable of withstanding fluid pressures up to at least about 500 psi. More typically, operating pressure may vary within the perfusion guidewire embodiment from about 2000 psi at the distal end to about 5000 psi at the proximal end, and thus preferred embodiments would be capable of withstanding such pressure. Such a system permits delivery of approximately 0.1 to 50 cc of fluid, such as oxygen superaturated fluid, per minute. With the high pressure delivery device described herein, such flows can be safely delivered to the patient with great accuracy of placement in tortuous vasculature and reduced risk of bubble formation or trauma to the vasculature.

Referring now to FIG. 2, a portion of proximal segment 10 of guidewire 108 is shown. Proximal segment 10 includes a first tube 12 which defines fluid lumen 14. Tube 12 is made of bio-compatible material, has the appropriate dimensions, and the appropriate burst strength, flexibility, torque transfer, and kink resistance characteristics, selectable by a person of skill in the art, for use in the particular intended application. Tube 12 may be coated over most of its length with a thin film of low friction, biocompatible coating 13, such as PTFE. Tube 12 and lumen 14 open at proximal end 16 for connection to source 102 shown in FIG. 1.

In one embodiment, tube 12 of proximal segment 10 is preferably a 304 stainless steel tube having an outside diameter of approximately 0.0140", an inside diameter of approximately 0.009", and a length of approximately 150 cm. Tube 12 preferably has a burst strength exceeding about 10,000 psi. Tube 12 preferably also has a 0.0002" to 0.0005" thick coating 13 of PTFE over its full length, except for a few centimeters at each end. If necessary, to avoid kinking during the initial part of a procedure, a support wire or stylet (not shown) may be inserted in tube 12. The support wire or stylet would be withdrawn before liquid is introduced into tube 12.

Referring now to FIG. 3, a preferred embodiment of the distal part of perfusion guidewire 108 is shown. The distal part includes transitional region 20, diffuser segment 40 and coil tip 50. Transitional region 20 comprises the region of perfusion guidewire 108 where the distal end of tube 12 connects to core wire 24, and to second tube 30. Transitional region 20 also includes the region wherein core wire 24 is provided with the appropriate cross sectional shape, length and diameter to provide desired handling characteristics. The distal end of core wire 24 is, in a preferred embodiment, ground with a series of taper and barrel grinds in order to provide a balance of stiffness, flexibility, pushability and torqueability to navigate the tortuosity of the vascular system as well as control fluid velocity of perfusion fluids delivered through the device. In particular, the profile of core wire 24 according to a preferred embodiment of the invention is designed, as explained below, to control the velocity of an oxygen supersaturated solution delivered at high pressure so as to reduce or eliminate bubble formation which may result from shear forces acting on the solution. Core wire 24 is preferably coated with a thin film of an appropriate hydrophilic coating which also helps reduce the possibility of bubble formation along its length. Based on the teachings of the present invention, a person of ordinary skill in the art may adapt the configuration of the core wire to different sizes of guidewires and to provide variations in handing characteristics.

In an exemplary embodiment, core wire 24 is approximately 30 cm long with a circular cross section. Central portion 24A of core wire 24 is the largest diameter at approximately 0.007". Central portion 24A preferably extends about 5.6" in length. Proximal to central portion 24A is tapered portion 24B (See FIG. 4). Tapered portion 24B tapers down to a diameter of approximately 0.004" over a distance of 0.54". Further proximal is attachment portion 24C (see FIG. 4). Moving distally from central portion 24A, core wire 24 includes tapered portion 24D, which tapers smoothly over about 1.4" from an outside diameter of approximately 0.007" down to an outer diameter of about 0.005". This is followed by untapered portion 24E, which extends for about 2.5". After that, distal portion 24F tapers over about 0.70" down to an outer diameter of about 0.0025". Moving further distally, portion 24G extends at about 0.0025" diameter through diffuser segment 40. The length of distal portion 24G is about 1.0".

Figure 4:
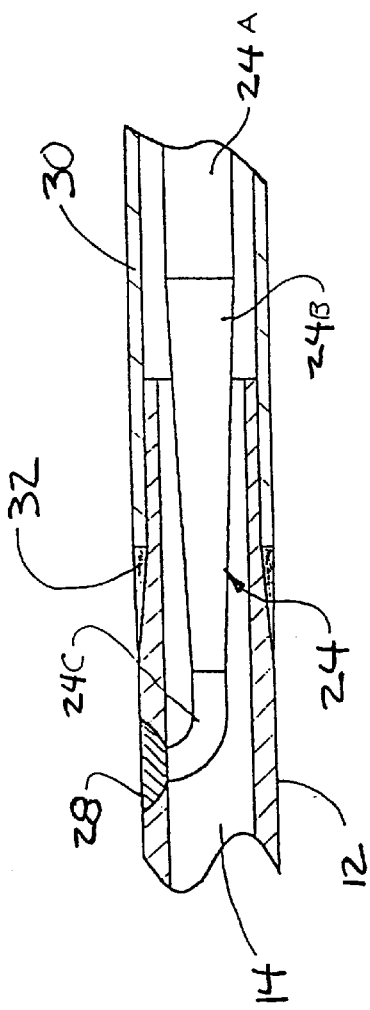
FIG. 4. is an enlarged, partial cross-sectional view of the transitional region, identified by circle 4 in FIG. 3.

The attachment of core wire 24 and second tube 30 to tube 12 is best illustrated, according to a preferred embodiment, in FIG. 4. A method for securing the core wire according to the invention is described below in connection with FIGS. 8A–8E. Attachment portion 24C of core wire 24 is welded or otherwise secured into opening 28 in the wall of tube 12. Portion 24C preferably maintains the approximate 0.004" diameter from portion 24B.

In order to provide for attachment of second tube 30 by epoxy adhesive 32, the distal end of tube 12 is tapered, preferably over about a distance of 0.25", to an outside diameter of about 0.0118". Second tube 30 is preferably a polyimide tube, having an outside diameter of approximately 0.0130" and an inside diameter of approximately 0.011". Second tube 30 has greater flexibility than tube 12. Other materials which exhibit desirable properties of flexibility and strength, such as polyester, may be used also. Second tube 30, in conjunction with core wire 24, provides an annular fluid path going forward from the attachment point of the core wire. The reduced outside diameter at the proximal end of tube 12 facilitates attachment of second tubular housing 30 while maintaining a low profile joint.

Referring again to FIG. 3, at the distal end of transitional region 20 is a connection to diffuser segment 40. The connection comprises a short outer support tube 32 secured by epoxy adhesive bonds 34 and 36 to both second tube and third tube 46 of diffuser segment 40. Diffuser segment 40 is preferably approximately 1.0–2.0 cm long, and third tube 46 defines a further extension of fluid lumen 14.

Tube 46 preferably may be made of polyimide which has excellent hoop strength as well as good burst strength and bondability. In the exemplary embodiment, so far described, third tube 46 has an inside diameter of about 0.006" and outside diameter of about 0.008". Fluid lumen 14 in this segment is also annular and of constant cross section due to the constant diameter of core wire portion 24G.

A plurality of outlet ports 44 are provided in third tube 46; however, the ports are shielded by diffusers 41. Diffusers 41 include sleeves 42 which surround tube 46. Ports 44 communicate with proximally directed fluid channels defined around housing 46 by sleeves 42. This creates a reverse flow which is generally parallel to the axis of perfusion guidewire 108. The design protects the vessel from trauma due to fluid impingement when the distal tip of perfusion guidewire 108 is placed, for example, deep into a small side branch of a coronary artery. Any number of diffusers may be utilized to provide a desired flow. According to the illustrated embodiment, four diffusers 41 are utilized, wherein the first three (illustrated in FIG. 5) vary slightly in construction from the fourth and distal-most diffuser (illustrated in FIG. 6).

Figure 5:
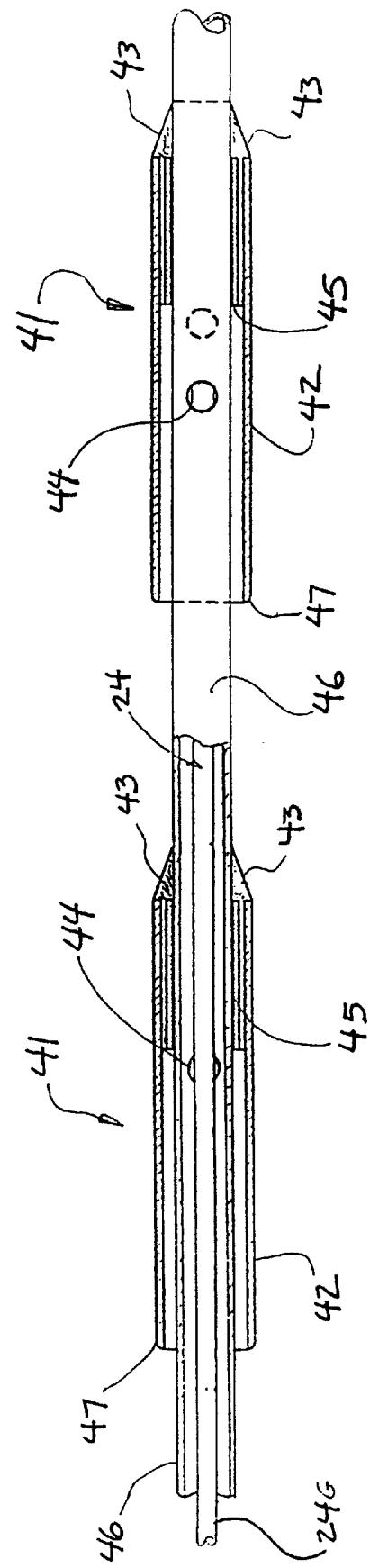
FIG. 5 is an enlarged, partial cross-sectional view of the diffuser segment of the perfusion guidewire identified by circle 5 in FIG. 3.

In the exemplary embodiment, illustrated in FIG. 5, each sleeve 42 is approximately 0.06" in length, with an outside diameter of approximately 0.014" and an inside diameter of approximately 0.012". Preferred materials are again polyimide and polyester. Each sleeve 42 is secured to tube 46 at the distal ends by epoxy joints 43, which is bevelled to be atraumatic. Annular polyimide bushing 45 also helps center the sleeves. The distance between the distal edge of one sleeve and the distal edge of the next sleeve in this embodiment is approximately 0.10". The proximal edge of the sleeves incorporate radius 47 to provide a non-catching, atraumatic profile. All joints exposed to supersaturated fluid flow have been filleted to provide a smooth flow path that eliminates bubble formation by filling in all sharp right angle edges exposed to the flow path. The angle of the fillets of the diffuser region assist in reducing the shear of the supersaturated oxygen solution during delivery.

Diffuser segment 40 divides the flow and reduces the fluid velocity, thereby providing an atraumatic, non-cavitating, cavitating, gentle, non-bubbling flow of high pressure oxygenated fluids. As shown in FIG. 6, fluid lumen 14 ends within tube 46 at the distal end of diffuser segment 40 where it is sealed by filler tube 52 and epoxy adhesive layers 48 and 49. Each of core wire portion 24G, filler tube 52, third tube 46 and epoxy layers 48 and 49 continue as a solid, but flexible, member into coil tip 50.

FIG. 7A illustrates an alternative embodiment wherein diffuser segment 40 includes distally open diffusers 41A which direct fluid distally and axially along the device to provide atraumatic fluid delivery. Other than the switch to a distal opening, diffusers 41A are preferably essentially the same as (mirror image of) diffusers 41 as described above. Coil tip 50 is also preferably as described below in connection with FIG. 7.

FIG. 7 shows coil tip 50 of perfusion guidewire 108. The material properties and dimensions of coil tip 50 are preferably selected to at least approximately match the physical properties, in particular handling characteristics, of standard coronary guidewires. At the proximal end of coil tip 50, filler tube 52, third tube 46 and epoxy layers 48 and 49 continue from the diffuser segment. Distal coil 54 is attached via epoxy adhesive 56, which fills between a number of the proximal coils as shown. Distal coil 54 serves as a compliant leading edge for the atraumatic and formable guidewire. The general requirements, construction, and dimensions of such a distal coil are well known to those skilled in the art. In a preferred embodiment, distal coil 54 is approximately 2 cm long with an outside diameter of about 0.014". Preferably distal coil 54 is radiopaque. A preferred material is platinum.

A length of stainless steel ribbon 58 is inserted into distal coil 54 until the proximal end of stainless steel ribbon 58 is positioned in the proximal end of distal coil 54. Distal coil 54 and stainless steel ribbon 58 are attached to filler tube 52 by epoxy joint 56. Stainless steel ribbon 58 is trimmed flush with the distal end of distal coil 54 and joined using silver solder 60 or other appropriate material. The distal end of core wire 24 is preferably finished off by flattening to approximately 0.001" thick.

Preferably, distal coil 54 is encapsulated in and filled by a flexible, soft durometer, medical grade, rubber material 62.

Preferred adhesives for material 62 are urethane adhesive and U.V. adhesives. A thin flexible film of a lubricous hydrophilic coating may then be applied over flexible material and to approximately 30 cm of the distal end of perfusion guidewire 108. Appropriate hydrophilic coatings, such as BSI PV01/PVP, are well known to those skilled in the art. Material helps eliminate bubble formation due to nucleation sites on the coil surface and between the coils by filling in the space between the coil wraps and captures the distal end of core wire 24. The soft durometer of material 62 allows the coil to be shaped while maintaining a hermetic seal between the individual coils.

The disclosed perfusion guidewire 108 may be inserted and used in the same manner as a standard coronary guidewire using a conventional torquing handle (not shown). Preferred embodiments of the invention exhibit substantially the same performance characteristics as a standard guidewire, and can be inserted and used with conventional instrumentation and techniques. Additionally, it is contemplated that features of the invention may be incorporated into non-guidewire fluid delivery devices without departing from the scope of the invention. For example, the diffuser segment may be readily adapted to other applications requiring delivery of fluids atraumatically through small flexible lumens. Also, the configuration of the coil tip described herein may be utilized with other fluid delivery guidewires or devices to reduce interference of the coils with fluid flow around the coil.

Figure 8A:
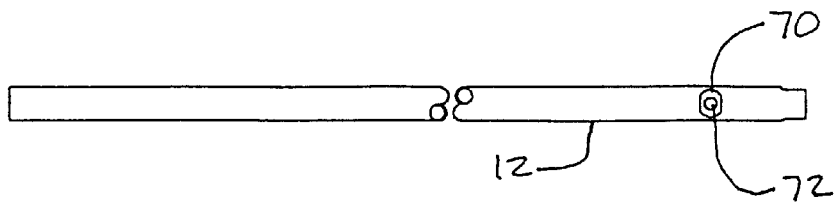
FIGS. 8A–E illustrate steps in attaching the core wire to the first tubular housing according to an embodiment of the invention.
Figure 8B:
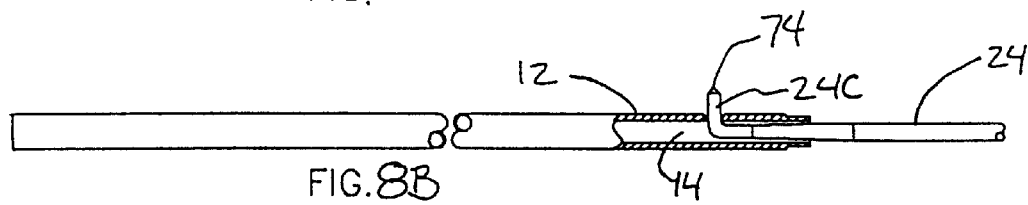
Figure 8C:
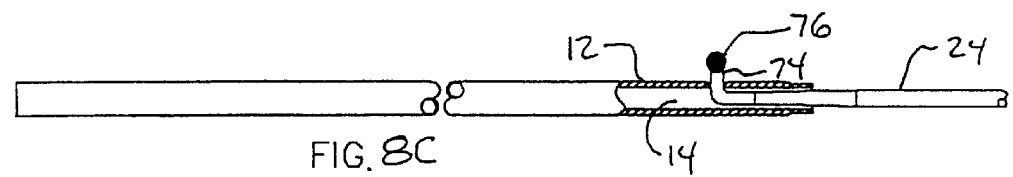
Figure 8D:
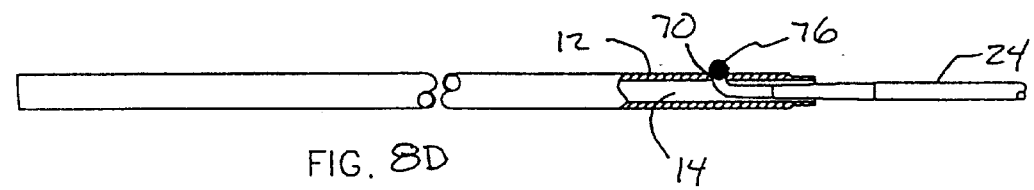
Figure 8E:
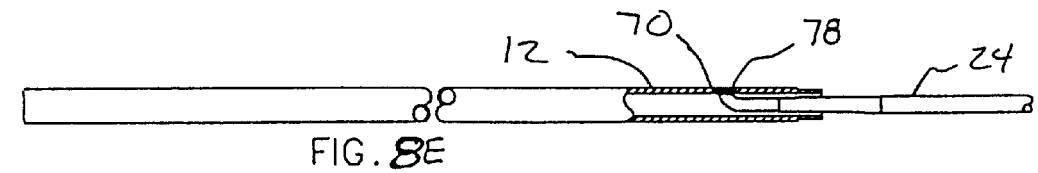

The connection of core wire 24 and tubular housing 12, as shown in FIG. 4, provides a smooth transition and flexibility and uniform transmission of a torque as between the tubular housing and core wire, such that the device, according to the present invention, exhibits handling characteristics substantially the same as standard guidewires. In particular, a smooth, even rotary action is required and provided by the guidewire of the present invention, even in a tortuous, vascular pathway. The connection, as disclosed, also provides a smooth transition with respect to fluid flow characteristics which is important when perfusing gas supersaturated fluids in order to minimize or prevent bubble formation. In particular, the connection of the core wire does not create sudden flow restrictions or pressure drops which may be presented in prior fluid delivery guidewires. A method for securing the core wire to the tubular housing, as shown in FIG. 4 is described below in connection with FIG. 8A–8E. Referring to FIG. 8A, notch 70 is cut into the wall of tubular housing 12 and a 0.0045" hole 72 is punched through the wall of tubular housing 12 centrally within notch 70. As shown in FIG. 8B, attachment portion 24C at the proximal end of core wire 24 is ground to a point at end 74. The point is then threaded through inner lumen 14 from the distal end and pushed up through hole 72. As illustrated in FIG. 8C, ball 76 is formed on end 74. Ball 76 preferably has a diameter of approximately 0.010" and may be formed, for example, by a laser welder. As shown in FIG. 8D, core wire 24 is pulled distally with respect to tubular housing 12 until ball 76 rests in notch 70. Finally, as shown in FIG. 8E, core wire 24 and tubular housing 12 are welded together, with welding material 78 filling notch 70. Any roughness may be ground smooth.

The described connection technique is one method for attaching the core wire to a tubular housing so as to achieve the advantages described above and combine high strength with a reliable and repeatable manufacturing process. This technique also permits the core wire to be attached directly to the tubular housing wall without an intervening structure, which could disrupt the flow characteristics and/or create discontinuities in torque and flexibility, while at the same time, permitting the core wire to become substantially centrally located within the tubular housing lumen, approximately at the point of attachment. Such central location reduces the length of tubing with an eccentric annular lumen.

The core wire attachment according to the present invention, as described above, may also be utilized advantageously in other devices, such as balloon catheters, including integral core wire construction. An example of such a balloon catheter is illustrated in FIG. 9. In this embodiment, core wire 24 is secured to first tubular housing 12, as shown in FIG. 4 and described above in connection with FIGS. 8A–8E. Second tubular housing 30 is attached to the first tubular housing as previously described. Balloon 80 may be formed from a third tubular housing 46A or alternatively may be formed directly from second tubular housing 30. Distal coil 54, with solder tip 60 and safety wire 58, are provided as previously described. Third tubular housing 46A is joined to core wire 24 at its distal end, and to coil spring 54 via epoxy joint 82. Epoxy 32 also joins the second and third tubular housings. Such a balloon may be formed by techniques known in the art and may include additional features such as a self-venting passage or holes for delivery of medication, which are described, respectively, in U.S. Pat. No. 4,793,350 and U.S. Pat. No. 5,087,244, each of which is incorporated by reference herein. Additionally, the distal coil of the balloon embodiment may incorporate filler material 62 if desired.

It is to be understood that the present invention has been described in terms of an exemplary embodiments. Thus, the invention is not limited to the specific embodiments depicted and described. Rather, the scope of the invention is defined by the appended claims.

What is claimed is:

1. A method for securing a core wire within a tubular housing in an apparatus for insertion into a human or animal body, comprising:

pushing an end of the core wire through a wall of the tubular housing from inside said housing;

forming an enlarged portion on the end of the core wire;

advancing the core wire to position the enlarged portion against the tubular housing;

securing the core wire within the wall of the tubular housing; and removing excess core wire and enlarged portion material from outside the tubular housing.

2. The method according to claim 1, wherein said pushing step comprises forming a hole in said wall and placing said core wire end through said hole.

3. The method according to claim 2, further comprising forming a notch on an outer surface of the tubular housing wall and forming said hole within said notch.

4. The method according to claim 3 wherein said advancing step comprises seating said enlarged portion within said notch.

5. The method according to claim 1, wherein said securing step comprises welding the core wire and enlarged portion into said housing wall.

6. The method according to claim 1, further comprising grinding the core wire with a series of taper and barrel grinds.

7. The method according to claim 1, further comprising coating the core wire with a thin film of hydrophilic coating.

8. The method according to claim 1, wherein the core wire is formed to have a circular cross section of varying diameter along its length.

9. The method according to claim 8, wherein the core wire is formed to have tapered and untapered portions along its length.

10. The method according to claim 1, further comprising forming an annular fluid path in the tubular housing between the core wire and the annular housing.

11. The method according to claim 1, further comprising attaching the core wire to a coil tip.

12. A method for attaching a core wire to a tubular housing in a fluid delivery guidewire comprising:

forming a side hole in the tubular housing;

passing an end of the core wire through the hole in the tubular housing;

melting a ball on the end of the core wire;

pulling the core wire to position the ball against the tubular housing; and welding the ball to fix the core wire in place.

13. The method according to claim 12, further comprising cutting a notch into an outer wall of the tubular housing.

14. The method according to claim 13, further comprising punching the hole centrally within the notch.

15. The method according to claim 12, further comprising grinding the end of the core wire to a point.

16. The method according to claim 12, further comprising threading the core wire through an inner lumen of the tubular housing and pushing the core wire through the hole formed in the tubular housing.

17. The method according to claim 12, further comprising forming the ball by a laser welder.

18. The method according to claim 13, further comprising pulling the core wire until the ball rests in the notch.

19. The method according to claim 18, further comprising welding the core wire and tubular housing together whereby welding material fills the notch.

20. The method according to claim 19, further comprising grinding smooth the welding material.

* * * * *